(12) United States Patent
Bentley et al.

(10) Patent No.: US 7,618,454 B2
(45) Date of Patent: Nov. 17, 2009

(54) TRANSFORAMINAL LUMBAR INTERBODY FUSION SPACERS

(75) Inventors: Ishmael Bentley, Eagen, MN (US); Steven J. Seme, Savage, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 283 days.

(21) Appl. No.: 11/295,858

(22) Filed: Dec. 7, 2005

(65) Prior Publication Data

US 2007/0129804 A1 Jun. 7, 2007

(51) Int. Cl.
 *A61F 2/44* (2006.01)
(52) U.S. Cl. .................. 623/17.11; 623/17.16
(58) Field of Classification Search .... 623/17.11–17.16
See application file for complete search history.

(56) References Cited

U.S. PATENT DOCUMENTS

| | | | |
|---|---|---|---|
| 5,961,554 A * | 10/1999 | Janson et al. | 623/17.16 |
| 6,143,035 A | 11/2000 | McDowell | |
| 6,187,043 B1 * | 2/2001 | Ledergerber | 623/8 |
| 6,245,108 B1 * | 6/2001 | Biscup | 623/17.11 |
| 6,296,664 B1 * | 10/2001 | Middleton | 623/17.15 |
| 6,491,724 B1 * | 12/2002 | Ferree | 623/17.11 |
| 6,562,072 B1 * | 5/2003 | Fuss et al. | 623/17.11 |
| 6,652,592 B1 | 11/2003 | Grooms et al. | |
| 6,696,073 B2 | 2/2004 | Boyce et al. | |
| 6,719,794 B2 | 4/2004 | Gerber et al. | |
| 6,851,430 B2 | 2/2005 | Tsou | |
| 6,942,697 B2 | 9/2005 | Lange et al. | |
| 6,942,698 B1 * | 9/2005 | Jackson | 623/17.16 |
| 7,060,073 B2 * | 6/2006 | Frey et al. | 606/85 |
| 7,291,170 B2 * | 11/2007 | Huppert | 623/17.11 |
| 2002/0022886 A1 * | 2/2002 | Fuss et al. | 623/17.11 |
| 2002/0077632 A1 | 6/2002 | Tsou | |
| 2002/0165612 A1 | 11/2002 | Gerber et al. | |
| 2003/0039676 A1 | 2/2003 | Boyce et al. | |
| 2003/0083747 A1 | 5/2003 | Winterbottom et al. | |
| 2003/0125739 A1 | 7/2003 | Bagga et al. | |
| 2003/0139813 A1 | 7/2003 | Messerli et al. | |
| 2004/0034428 A1 | 2/2004 | McKay | |
| 2004/0158328 A1 | 8/2004 | Eisermann | |
| 2004/0167538 A1 | 8/2004 | Gerber et al. | |
| 2004/0172133 A1 | 9/2004 | Gerber et al. | |
| 2004/0186572 A1 | 9/2004 | Lange et al. | |
| 2004/0220668 A1 | 11/2004 | Eisermann et al. | |

(Continued)

FOREIGN PATENT DOCUMENTS

EP     1 290 985 A2     3/2003

(Continued)

*Primary Examiner*—Pedro Philogene
(74) *Attorney, Agent, or Firm*—Crompton, Seager & Tufte, LLC.

(57) ABSTRACT

An implant for spinal fusion that includes a top surface and a bottom surface opposing the top surface. An anterior surface extends from the top surface to the bottom surface and a posterior surface extends from the top surface to the bottom surface. The implant includes a first end, a second end, and a means for promoting spinal fusion. The implant may further include one or more of a cavity and a trough wherein bone growth material may be backed before or after the implant is inserted into the spine.

16 Claims, 9 Drawing Sheets

U.S. PATENT DOCUMENTS

| | | |
|---|---|---|
| 2004/0220670 A1 | 11/2004 | Eisermann et al. |
| 2004/0225365 A1 | 11/2004 | Eisermann et al. |
| 2004/0225366 A1 | 11/2004 | Eisermann et al. |
| 2004/0267366 A1 | 12/2004 | Kruger |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0038511 A1 | 2/2005 | Martz et al. |
| 2005/0049703 A1 | 3/2005 | Lee |
| 2005/0096745 A1 | 5/2005 | Andre et al. |

FOREIGN PATENT DOCUMENTS

| | | |
|---|---|---|
| EP | 1 290 985 A3 | 3/2003 |
| EP | 1 430 858 A1 | 6/2004 |
| EP | 1 468 652 A1 | 10/2004 |
| WO | WO 02/089712 A1 | 11/2002 |
| WO | WO 2004/043291 A2 | 5/2004 |

\* cited by examiner

TRANSFORAMINAL LUMBAR INTERBODY FUSION SPACERS

TECHNICAL FIELD

The present invention relates generally to spinal implants. More particularly, this invention relates to spinal implants for insertion into a spinal intervertebral disc space to promote spinal fusion.

BACKGROUND

Spinal fusion surgical procedures involve joining or fusing two or more vertebrae together. The procedure typically includes using bone graft or bone growth material to promote fusion. The bone material and a spinal implant (also known as a spacer or cage) are inserted in the intervertebral space and take the place of an intervertebral disc. The spacer bears the load transferred from one vertebra to the next vertebra, and in conjunction with the bone graft material, acts to fuse the vertebrae together. Spinal fusion surgery can be used to treat spinal fractures, lumbar disc herniation, scoliosis, and other spinal disorders.

Several procedures are known for implanting spinal implants. The posterior lumbar interbody fusion ("PLIF") procedure involves making an incision in the patient's back and retracting the spinal muscles to allow access to the vertebral space. Next, the lamina is removed to allow visualization and access to the nerve roots. The affected intervertebral disc is removed and the space prepared for the implant. The bone graft or bone growth material and the spinal implant are inserted into the disc space to promote fusion. The transforaminal lumbar interbody fusion ("TLIF") procedure is a modification of the PLIF procedure. During the TLIF procedure, the incision is made to the side of the spinal canal through a midline incision in the patient's back. This reduces the amount of muscle retraction and nerve manipulation required. In the anterior lumbar interbody fusion ("ALIF") procedure, the incision is made in the lower abdominal area. This procedure may involve cutting through the lower abdominal muscles.

A number of spinal implants are known in the art. However, there is a need for an improved spinal fusion spacer that facilitates improved packing of bone material or bone growth promoter in and around the spacer in the disc space while minimizing the invasiveness of the implantation procedure.

SUMMARY

A spinal bone implant comprising a top surface and a bottom surface opposing the top surface. An anterior surface extends from the top surface to the bottom surface and a posterior surface extends from the top surface to the bottom surface. The implant includes a first end, a second end, and a means for promoting bone fusion.

One embodiment of the present invention may include a transforaminal lumbar intervertebral spacer with a body including an anterior surface opposite a posterior surface and defining a curvilinear axis between a first end and a second end whereby the distance between the anterior surface and the posterior surface varies across the curvilinear axis, the body further including a trough formed on at least one of the anterior and posterior surfaces.

Another embodiment of the present invention may include a method of implanting a vertebral implant into an intervertebral space to achieve spinal fusion, the steps including creating an intervertebral space between a first vertebra and a second vertebra, inserting a vertebral implant, the vertebral implant including a body with an anterior surface opposite a posterior surface and defining a curvilinear axis between a first end and a second end whereby the distance between the anterior surface and the posterior surface varies across the curvilinear axis, the body further including a trough formed on at least one of the anterior and posterior surfaces, and packing the trough with a bone growth material.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
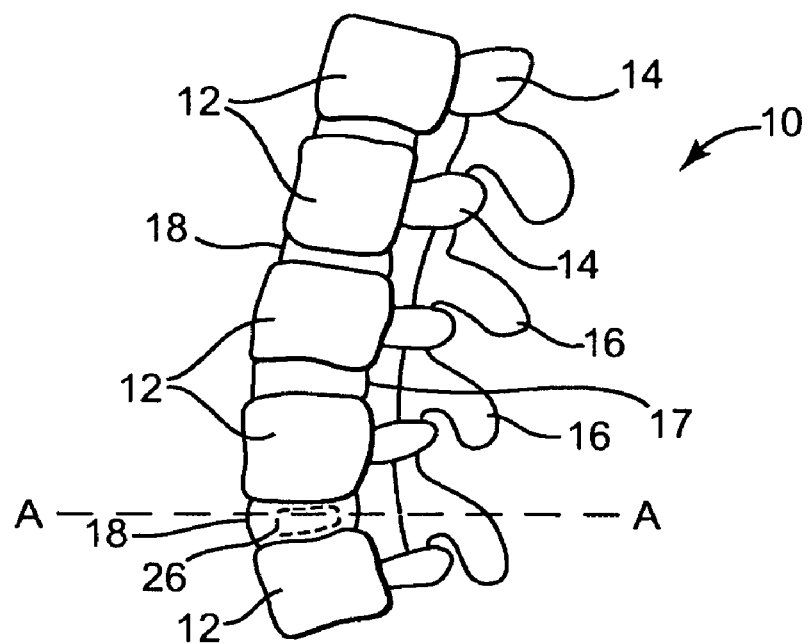
FIGS. 1A-1B show various views of the lumbar spine.
Figure 1B:
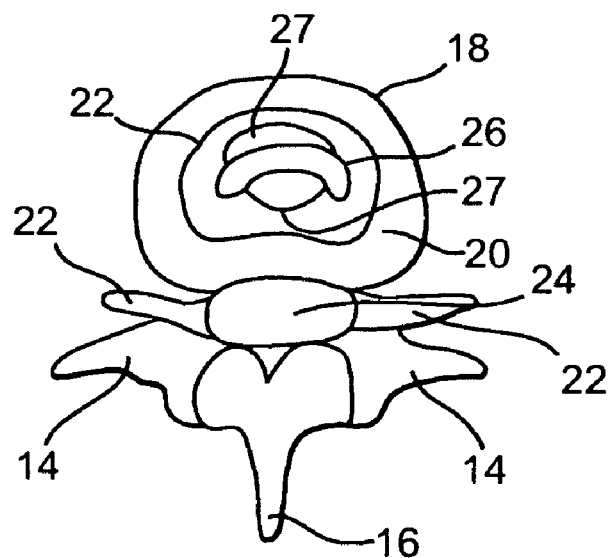

FIG. 1A shows a side view of the lumbar region 10 with a spacer 26 implanted. The lumbar region 10 includes the lumbar vertebrae 12, transverse processes 14, and spinous processes 16. The intervertebral foramen 17 and the intervertebral discs 18 are interposed between the lumbar vertebrae 12. FIG. 1B is a cross section of the lumbar region 10 of FIG. 1A taken across the section A-A. As shown in FIG. 1B, the intervertebral disc 18 includes the annulus fibrosus 20 surrounding the nucleus pulposus 22. Nerve roots 22 extend from either side of the spinal cord 24. FIG. 1B further shows a bone growth material 27 packed around the spacer 26.

Figure 2:
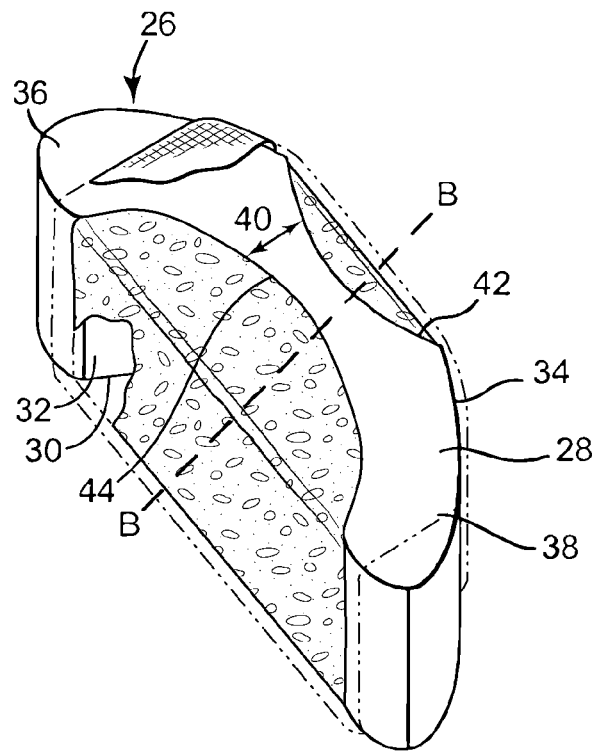
FIG. 2 shows a perspective view of a transforaminal lumbar intervertebral spacer according to one embodiment of the present invention.

FIG. 2 shows a perspective view of one embodiment of a transforaminal lumbar intervertebral ("TLIF") spacer 26 according to one embodiment of the present invention. The spacer of FIG. 2 may include a top surface 28, a bottom surface 30 substantially opposed to the top surface 28, a posterior surface 32 extending from the top surface 28 to the bottom surface 30, and an anterior surface 34 extending from the top surface 28 to the bottom surface 30. A first end 36 may be located at one end of the spacer 26 and a second end 38 may be located at the opposing end. The spacer 26 further includes a central axis B-B extending from the posterior surface 32 to the anterior surface 34 and centrally located between the first end 36 and the second end 38. The anterior surface 34 has a substantially convex shape, which allows the spacer 26 to be guided with respect to the curvature of the annulus fibrosus 20 during insertion.

As shown in FIG. 2, the distance 40 between the posterior surface 32 and the anterior surface 34 varies across the length of the spacer 26. The distance 40 is less at the central axis B-B than it is at the first end 36 or the second end 38. In the embodiment shown in FIG. 2, the decreased thickness may be created by a section or trough 42 created in the anterior surface 34 and by a section or trough 44 created in the posterior surface 32. A bone growth material 45 can be packed in the troughs 42, 44. Bone growth material 45 may include bone growth inducing material, bone grafting material, or any other type of material that promotes or encourages bone growth or bone fusion. The bone growth material 45 can be packed in the troughs 42, 44 prior to insertion into a patient, and the spacer 26 then inserted into a patient. A sheet or netting material 47 may be optionally used to more securely pack the bone growth material 45 to the spacer 26. For example, the sheet or netting material 47 may be at least partially wrapped abound an assembly of a spacer 26 packed with the bone growth material. The sheet or netting material 47 can be a variety of materials suitable for temporary or permanent implantation. For example, a plastic sheet can be used to wrap the assembly for insertion into the disc space and removed after the assembly has been inserted. Alternatively, the sheet or netting material can be a biocompatible material or a material absorbable by the patient body and left inside the disc space with the assembly.

Alternatively, the bone growth material may be packed in the troughs 42, 44 after the spacer 26 has been inserted, or both before and after insertion. The packing of the bone growth material promotes spinal fusion. The spacer 26 retains enough material at the ends 36, 38 to transfer the load from one vertebra 12 to the next vertebra 12. The decreased thickness 40 also allows for reduced retraction of the nerve root or spinal cord once the first end 36 has been inserted into the patient.

Figure 3:
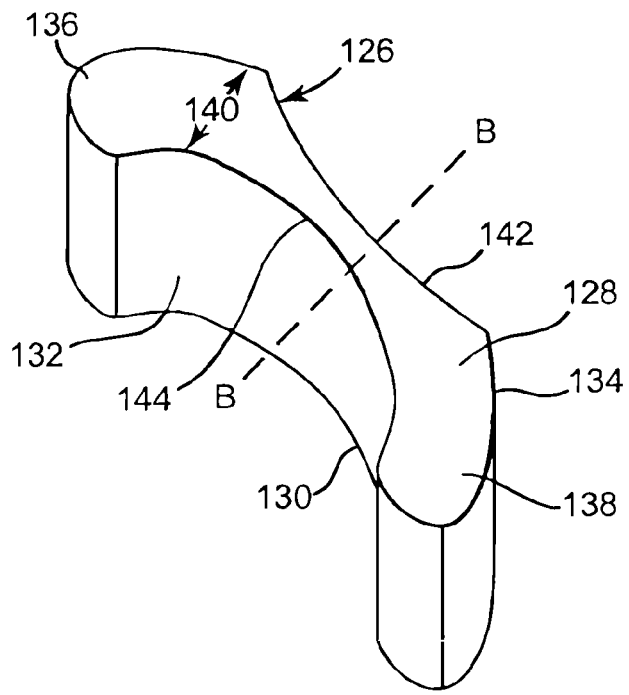
FIG. 3 shows a perspective view of a transforaminal lumbar intervertebral spacer according to one embodiment of the present invention.

FIG. 3 shows another embodiment of the present invention. In FIG. 3, the troughs 142, 144 may have a larger radius of curvature than the troughs 42, 44 of FIG. 2. Larger troughs 142, 144 may result in a larger difference between the thickness 140 at the central axis B-B compared to the thickness at the ends 36, 38. While both troughs 142, 144 may have increased radius of curvatures in FIG. 3, in an alternative embodiment, either trough 142 or trough 144 could have an increased radius. The troughs 142, 144 provide space for the backing of bone growth or bone graft material, thus promoting spinal fusion.

Figure 4:
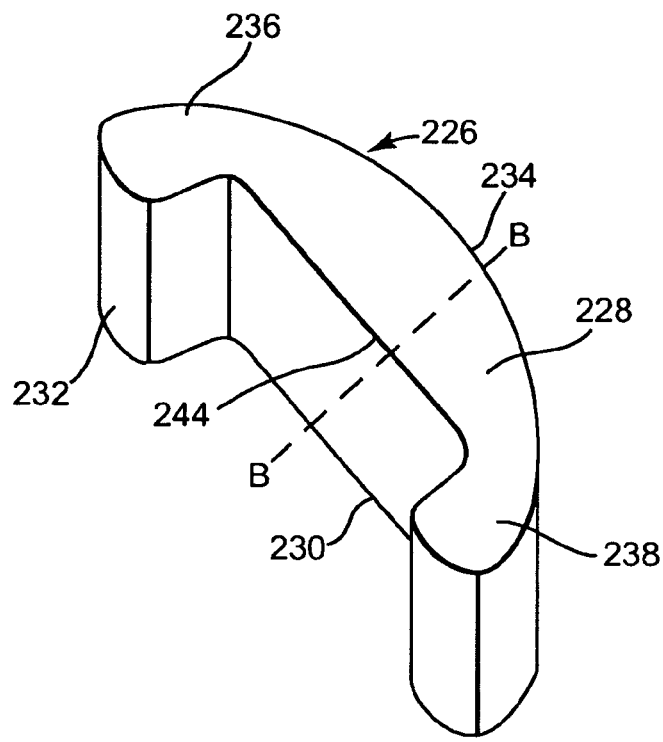
FIG. 4 shows a perspective view of a transforaminal lumbar intervertebral spacer according to one embodiment of the present invention.
Figure 5:
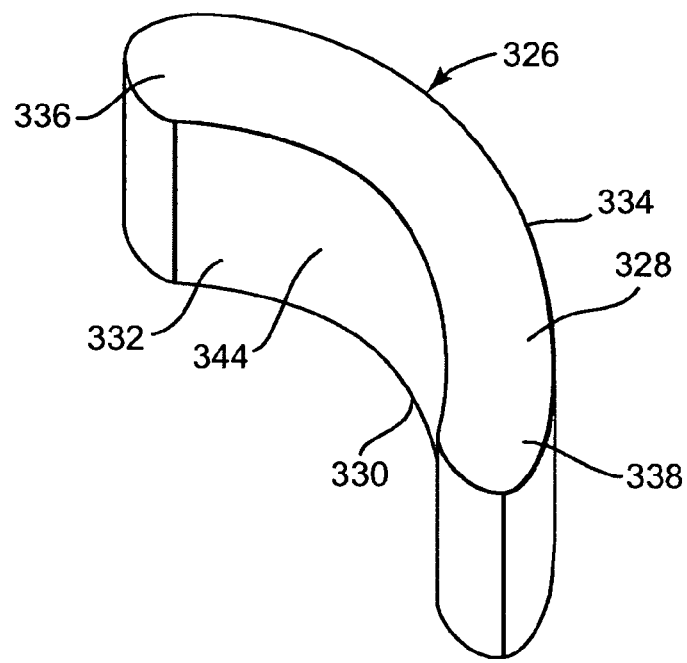
FIG. 5 shows a perspective view of a transforaminal lumbar intervertebral spacer according to one embodiment of the present invention.

FIG. 4 shows another embodiment of the present invention. In this embodiment, the spacer 226 may have a convex anterior surface 234 and a substantially planar posterior surface 232. The trough 244 in the posterior surface 232 may have a substantially rectangular cross section. The trough 244 may provide a space for backing bone growth material into the spacer 226, either before insertion into the patient, after insertion, or both. The trough 244 thus promotes spinal fusion. FIG. 5 shows yet another embodiment of the present invention. In FIG. 5, the spacer 326 may have a substantially concave posterior surface 332 and a substantially convex anterior surface 334. The concave nature of the posterior surface 332 may create a trough 344 that allows for packing of bone growth material into the space created by the concavity, promoting spinal fusion.

Figure 6:
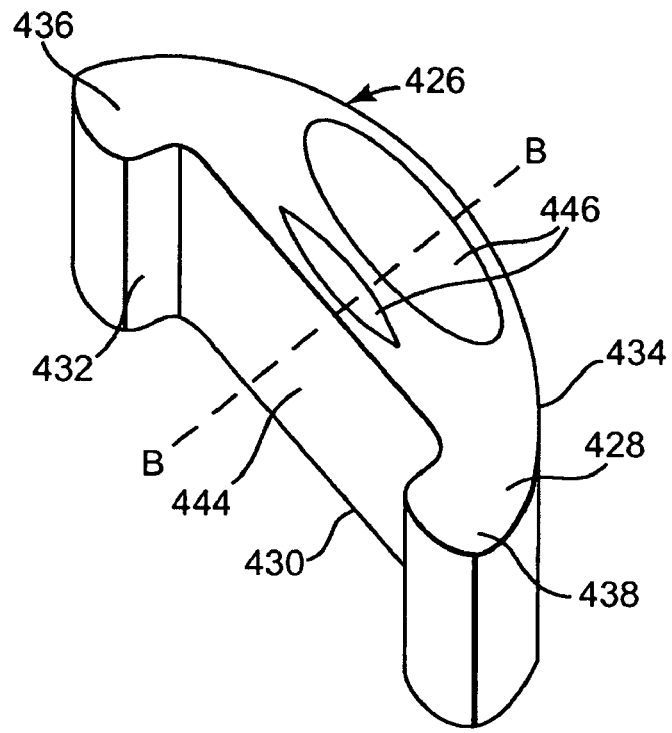
FIG. 6 shows a perspective view of a transforaminal lumbar intervertebral spacer according to one embodiment of the present invention.
Figure 7:
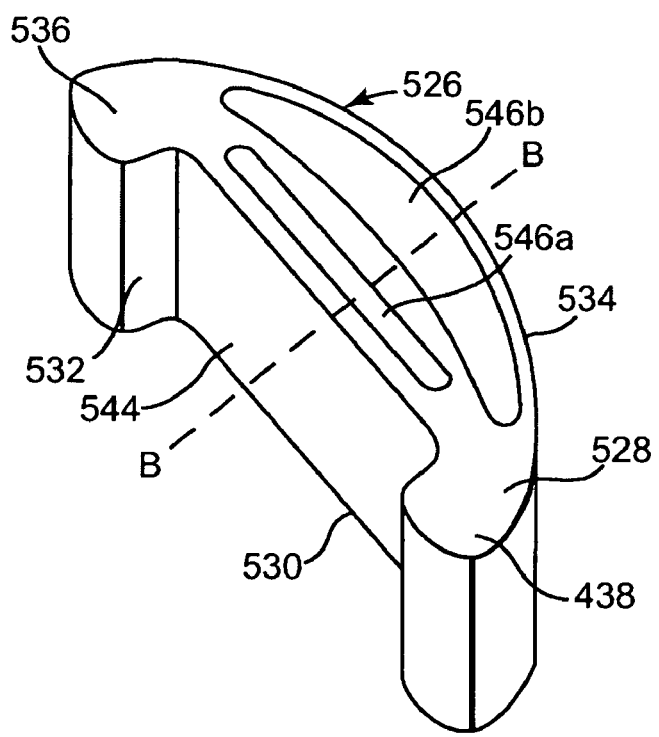
FIG. 7 shows a perspective view of a transforaminal lumbar intervertebral spacer according to one embodiment of the present invention.
Figure 8:
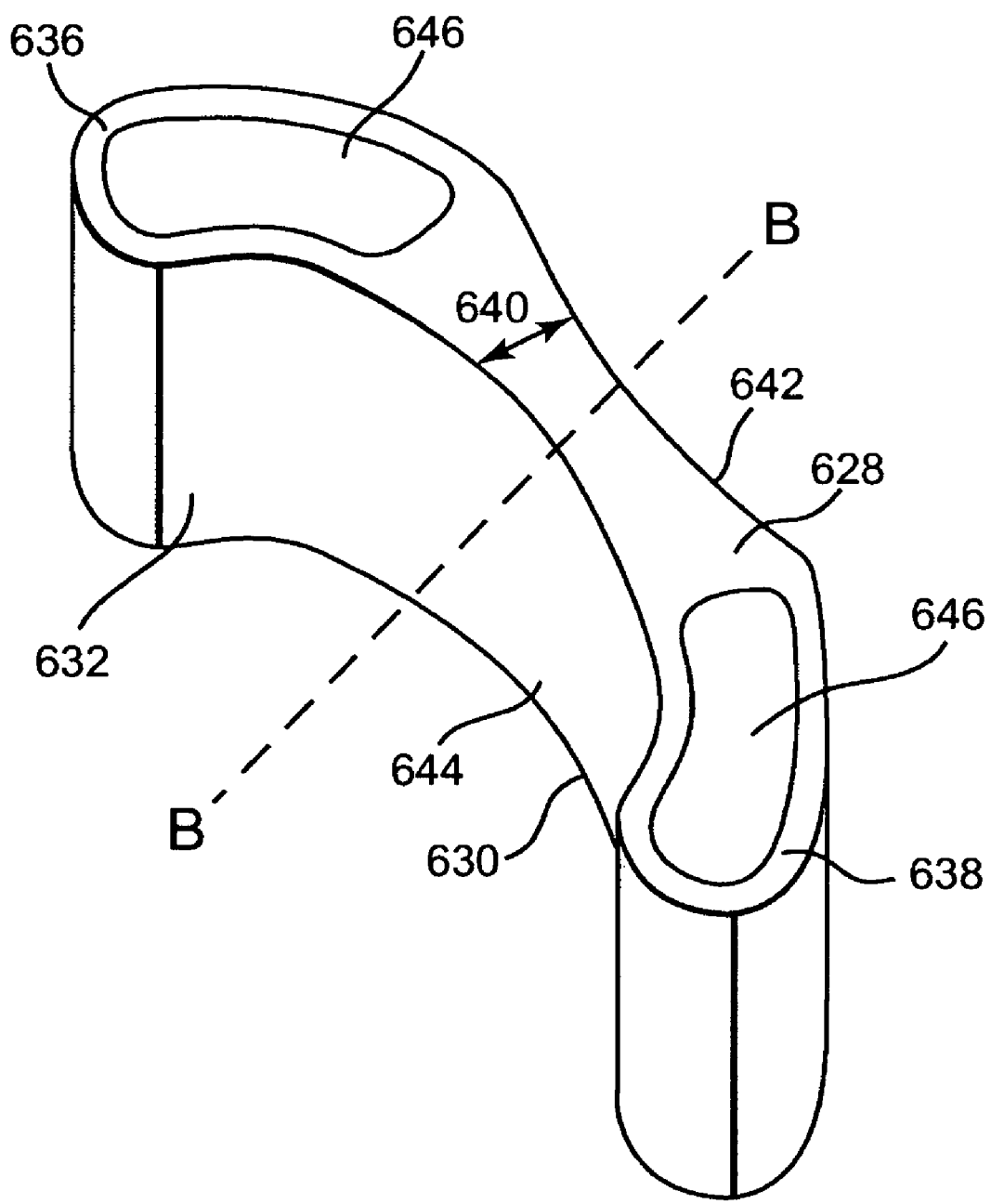
FIG. 8 shows a perspective view of a transforaminal lumbar intervertebral spacer according to one embodiment of the present invention.

FIG. 6 shows another embodiment of the present invention. As shown in FIG. 6, the spacer 426 may have a substantially convex anterior surface 434, a posterior surface 432, and a trough 444 located in the posterior surface 432. Bone growth or bone graft material may be packed in trough 444 either before insertion of the spacer 426, after insertion, or both. This packing promotes spinal fusion. The spacer 426 may further include one or more channels 446 extending from the top surface 428 to the bottom surface 430. These channels 446, which may be referred to as a cavity or cavities, may allow for additional packing of bone growth or bone graft material into the spacer 426, further promoting spinal fusion. Two channels 446 are shown in FIG. 6, each having an ovular shape, but the spacer 426 may alternatively have any number of channels 446 having any shape. As shown in FIG. 7, the spacer 526 may have one channel 546a, the channel 546a having a substantially rectangular cross-section, and another channel 546b, the channel 546b having a substantially semi-circular cross-section. The channels 546a, 546b may allow for packing of bone growth material and therefore promote spinal fusion. The trough 544 may further promote spinal fusion by providing a space for additional bone growth material. Similarly, the TLIF spacer 626 of FIG. 8 may include two channels 646 for bone growth material, each channel 646 located at the ends 636, 638. The channels 646 and troughs 642, 644 may allow for packing of bone growth material and therefore promote spinal fusion.

Figure 9:
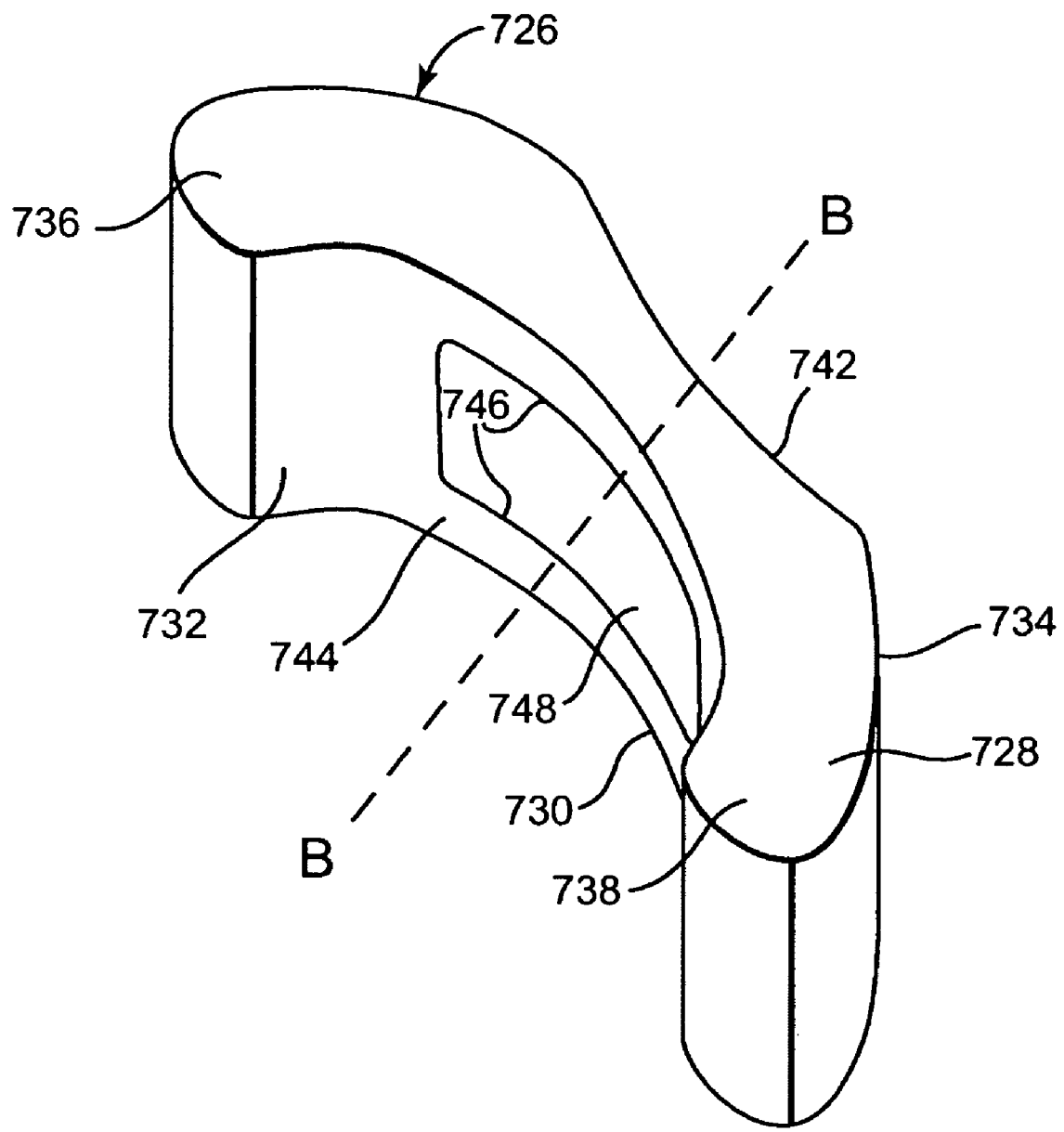
FIG. 9 shows a perspective view of a transforaminal lumbar intervertebral spacer according to one embodiment of the present invention.
Figure 10:
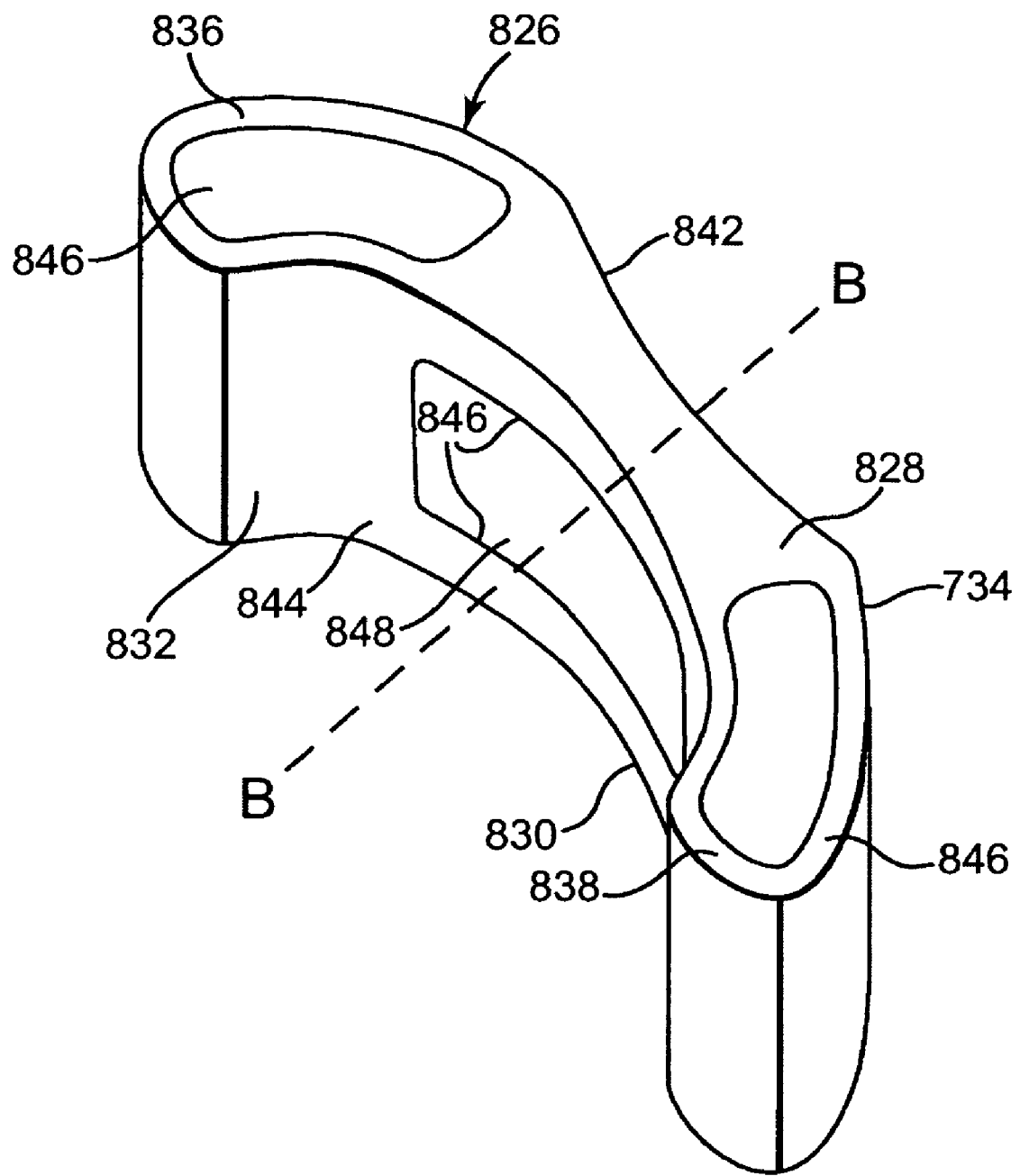
FIG. 10 shows a perspective view of a transforaminal lumbar intervertebral spacer according to one embodiment of the present invention.

FIG. 9 shows an additional embodiment of the present invention. In the embodiment shown in FIG. 9, the TLIF spacer 726 may include a horizontal channel 748 extending from the anterior surface 734 to the posterior surface 732. This horizontal channel 748 may provide a space for bone growth or bone graft material, thus promoting fusion in a horizontal direction as well as in a vertical direction through troughs 742, 744. Similarly, the TLIF spacer 826 of FIG. 10 may include two channels 846 located at the ends 836, 838, and a horizontal channel 848. The channel 848, channels 846, and troughs 842 and 844 all allow for packing of bone growth material, thus promoting spinal fusion.

Figure 11:
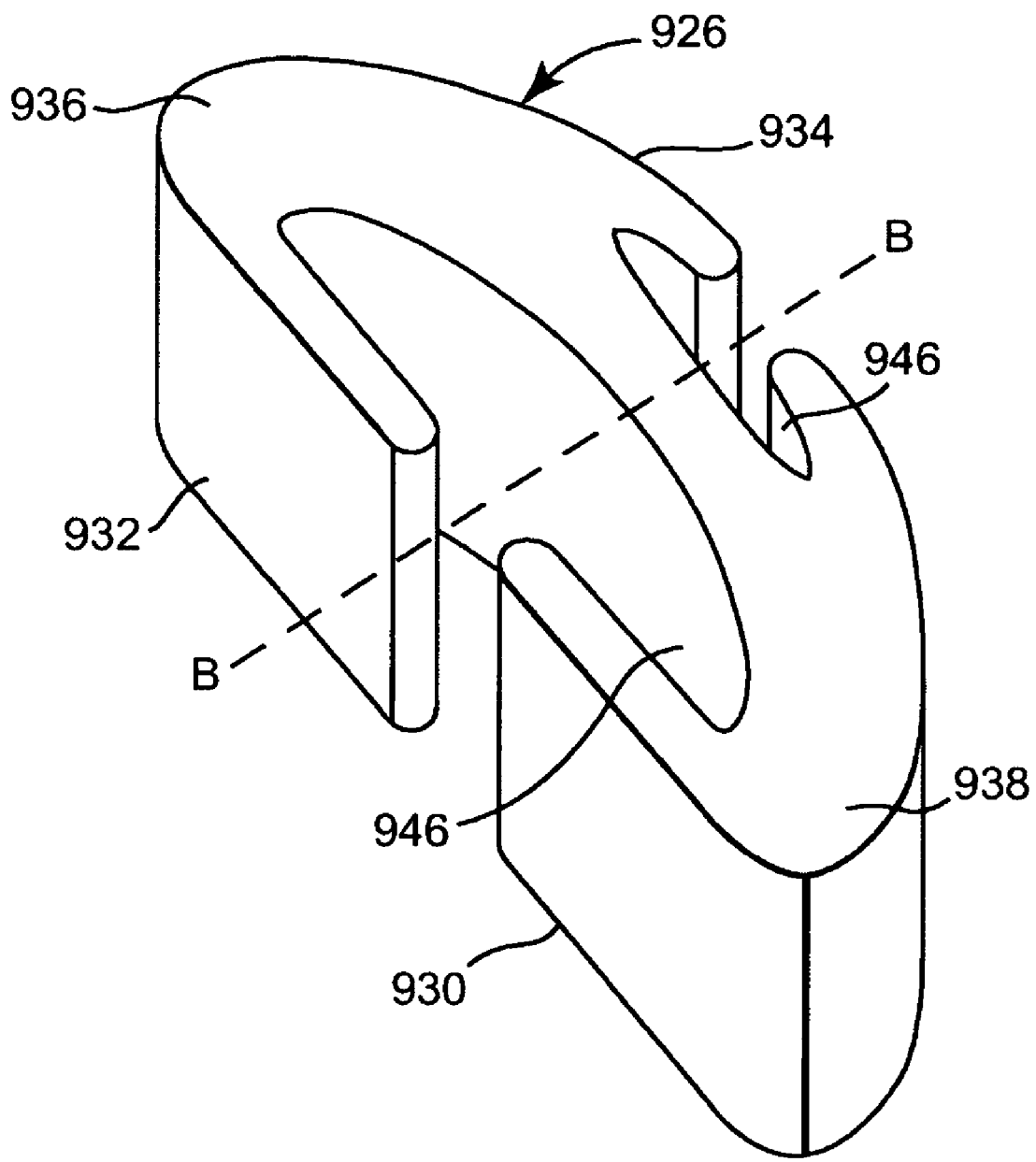
FIG. 11 shows a perspective view of a transforaminal lumbar intervertebral spacer according to one embodiment of the present invention.
Figure 12:
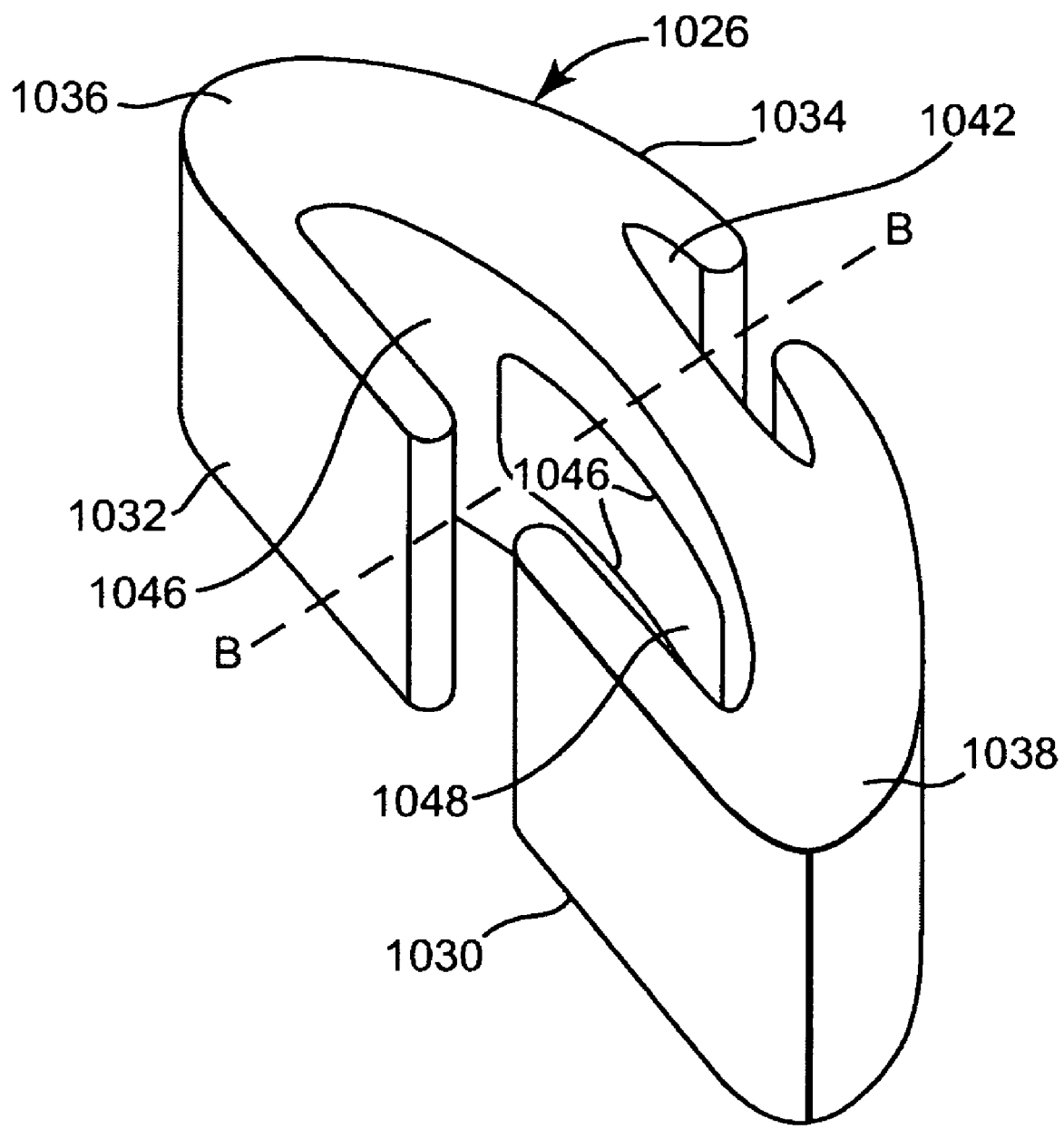
FIG. 12 shows a perspective view of a transforaminal lumbar intervertebral spacer according to one embodiment of the present invention.

FIG. 11 shows yet another embodiment of the present invention. In this embodiment, the channels 946 are not completely surrounded by spacer 926 material. The open construction of the channels 946 may allow bone growth or bone graft material to be packed in the channels 946 before insertion of the spacer 926 into the patient, or after insertion, or both. This packing promotes spinal fusion. An alternative spacer 1026 is shown in FIG. 12. The spacer 1026 may include the open channels 1042 for promoting fusion in the vertical direction and also includes a horizontal channel 1048 for promoting bone fusion in the horizontal direction.

The horizontal channels 748, 848 and 1048 in the above illustrative embodiments may facilitate improved bone growth. The horizontal beams 746, 848 and 1046 may have smaller heights than the total heights of the spacers and may be much more flexible vertically than the remaining portions of the spaces that support the vertebrae. The increased flexion may cause more stress on any bone graft inside the channels 748, 848 and 1048, respectively, and therefore result in increased mechanical stimulation of bone growth.

The spacers disclosed above may have any height suitable for insertion into the intervertebral space. In one embodiment, the spacers may have a height of between 8 and 20 millimeters. The length of the spacers may vary as needed to fit into the nucleus pulposus 23. The spacers may be constructed of bone, titanium, carbon fiber reinforced polymer, polyetheretherketone (PEEK™), carbon fiber reinforcing polymer strops (CFRP), radiolucent material, or any other biocompatible material having the required strength. In an alternative embodiment, the distance 40 from the posterior surface 32 to the anterior surface 34 of the first end 36 can be less than the distance 40 at the second end 38, allowing the spacer 26 to pack bone material around itself as it is inserted into the nucleus pulposus 23. Any number of vertical channels, horizontal channels, and troughs can be used for packing of bone growth material to promote bone fusion.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

What is claimed is:

1. A transforaminal lumbar intervertebral spacer comprising:
   a body including an anterior surface opposite a posterior surface and defining a curvilinear axis between a first end and a second end whereby a distance between the anterior surface and the posterior surface varies across the curvilinear axis, the body further including a partially enclosed cavity formed in each of the anterior and posterior surfaces, the cavity extending between a top surface and a bottom surface of the body and defining a space wherein bone growth material can be packed.

2. The spacer of claim 1 wherein the posterior surface is concave.

3. The spacer of claim 1 wherein the anterior surface is concave.

4. The spacer of claim 1 wherein the top surface and the bottom surface are generally parallel.

5. The spacer of claim 1 wherein each cavity further comprises an opening in at least one of the bottom surface and the top surface.

6. A method of implanting a vertebral implant into an intervertebral space to achieve spinal fusion, comprising:
   creating an intervertebral space between a first vertebra and a second vertebra;
   inserting a vertebral implant, the vertebral implant including a body with an anterior surface opposite a posterior surface and defining a curvilinear axis between a first end and a second end whereby the distance between the anterior surface and the posterior surface varies across the curvilinear axis, the body further including a trough formed in each of the anterior and posterior surfaces;
   packing the trough with a bone growth material; and
   covering at least a portion of the bone growth material and at least a portion of the implant body with a sheet material before inserting the vertebral implant into the intervertebral space, the sheet material being wrapped around the bone growth material and the vertebral implant to retain the bone growth material in the vertebral implant.

7. The method of claim 6 further comprising mechanically stimulating bone growth in the disc space.

8. The method of claim 7 wherein mechanical stimulation is achieved by flexing a portion of the implant body.

9. The method of claim 6 wherein the inserting the vertebral implant further comprises inserting the vertebral implant transforaminally.

10. The method of claim 6 wherein the inserting the vertebral implant further comprises inserting the vertebral implant such that the anterior surface substantially faces the anterior of the patient.

11. An intervertebral spinal fusion prosthesis comprising:
   a top surface wherein a middle portion extends between a first end and a second end;
   a bottom surface substantially opposed to the top surface,
   a posterior surface extending from the top surface to the bottom surface, an anterior surface extending from the top surface to the bottom surface opposite to the posterior surface whereby a distance between the posterior surface and the anterior surface is greater at the first end and the second end than at the middle portion; and
   a partially enclosed cavity formed in each of the anterior and posterior surfaces, the cavity extending between the top and bottom surfaces of the body and defining a space wherein bone growth material can be packed.

12. The spinal fusion prosthesis of claim 11 further comprising wherein the posterior surface is concave.

13. The spinal fusion prosthesis of claim 11 wherein the anterior surface is concave.

14. The spinal fusion prosthesis of claim 11 wherein at least one of the cavities further comprises an opening in the anterior surface.

15. The spinal fusion prosthesis of claim 11 wherein at least one of the cavities further comprises an opening in the posterior surface.

16. The spinal fusion prosthesis of 11 wherein the spinal implant further comprises a sheet wrapped around the prosthesis and gone graft material to retain the bone grafter material in the cavity.

* * * * *

UNITED STATES PATENT AND TRADEMARK OFFICE
CERTIFICATE OF CORRECTION

PATENT NO.       : 7,618,454 B2                                Page 1 of 1
APPLICATION NO. : 11/295858
DATED            : November 17, 2009
INVENTOR(S)      : Bentley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 513 days.

Signed and Sealed this

Twenty-sixth Day of October, 2010

David J. Kappos
*Director of the United States Patent and Trademark Office*